United States Patent [19]

Andrews

[11] Patent Number: 4,741,698
[45] Date of Patent: May 3, 1988

[54] SUBPERIOSTEAL IMPANT WITH DETACHABLE BAR AND METHOD FOR ITS IMPLANTING

[75] Inventor: Douglas V. Andrews, Pataskala, Ohio

[73] Assignee: Andrews Ceramic Laboratory, Inc., Columbus, Ohio

[21] Appl. No.: 849,379

[22] Filed: Apr. 8, 1986

[51] Int. Cl.⁴ .............................................. H61C 8/00
[52] U.S. Cl. .................................................. 433/173
[58] Field of Search ........................ 433/173, 175, 176

[56] References Cited

U.S. PATENT DOCUMENTS

| | | | |
|---|---|---|---|
| 2,644,231 | 7/1953 | Brennan | 433/173 |
| 3,514,858 | 6/1970 | Silverman | 32/2 |
| 3,641,671 | 2/1972 | Roberts | 32/10 A |
| 3,748,739 | 7/1973 | Thibert | 32/10 A |
| 3,889,375 | 6/1975 | Roberts | 32/10 A |
| 4,202,099 | 5/1980 | Roberts | 433/176 |
| 4,253,833 | 3/1981 | Edelman | 433/173 |
| 4,370,134 | 1/1983 | Roberts | 433/173 |
| 4,511,335 | 4/1985 | Tatum | 433/173 |
| 4,516,937 | 5/1985 | Bosker | 433/173 |

FOREIGN PATENT DOCUMENTS 2853638  6/1979  Fed. Rep. of Germany ...... 433/173

*Primary Examiner*—Robert Peshock
*Attorney, Agent, or Firm*—Mueller and Smith

[57] ABSTRACT

Disclosed is an improved dental implant for a denture which comprises a frame which is attachable to the mandibular or maxillary bone, said frame bearing bar retention means; a detachable bar having complementary bar retention means for removably attaching said detachable bar to said frame; and denture bearing denture bar retention for attaching said denture to said detachable bar.

23 Claims, 4 Drawing Sheets

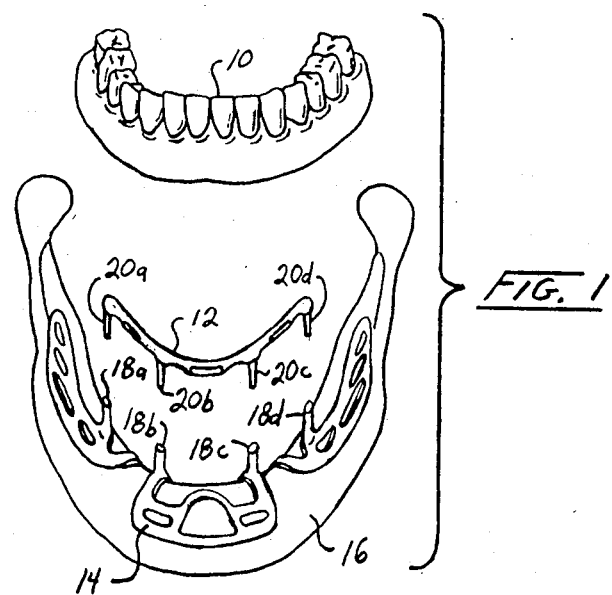
FIG. 1
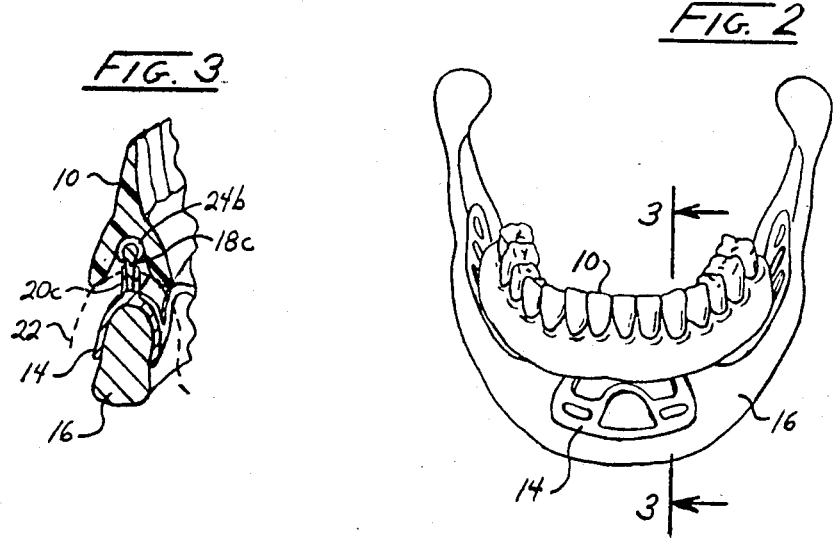
FIG. 3
FIG. 2
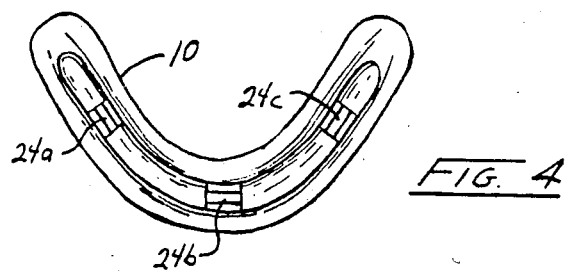
FIG. 4

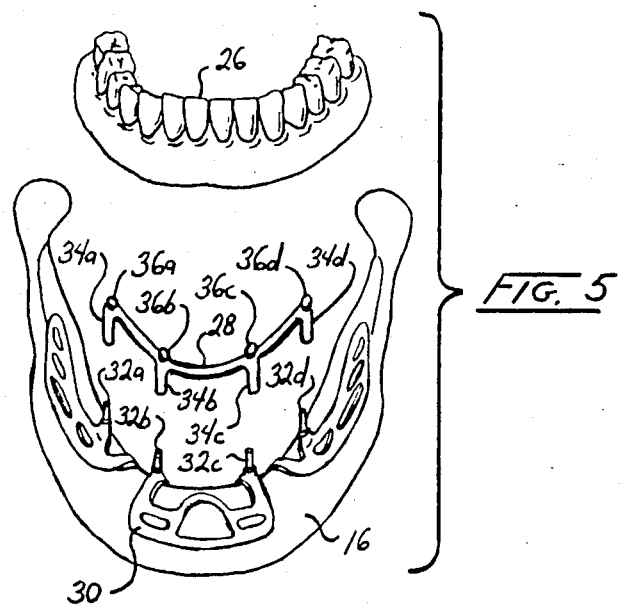
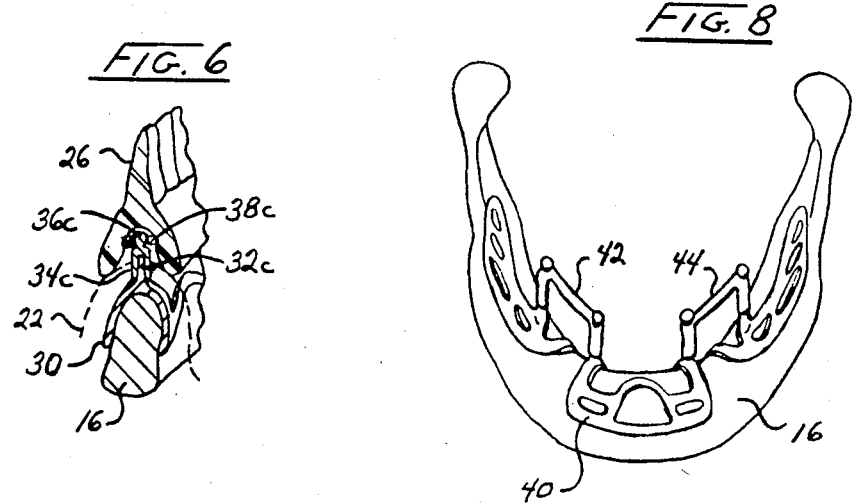
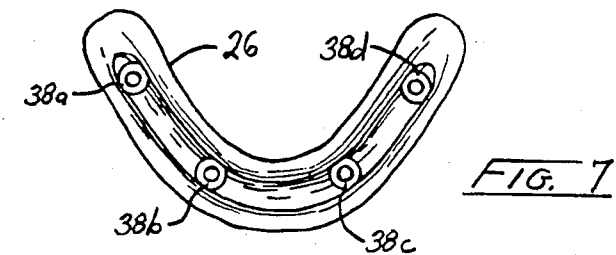

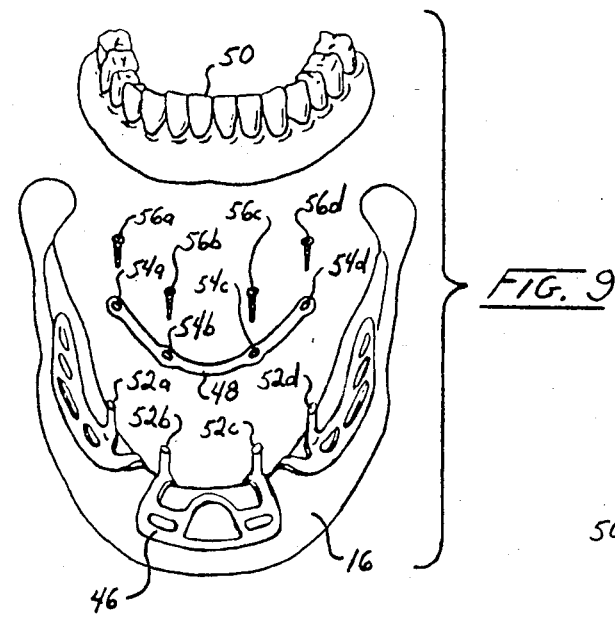
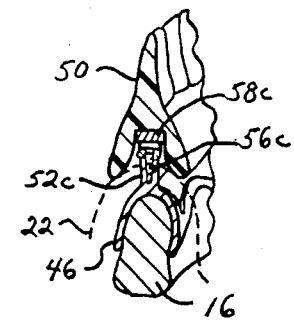
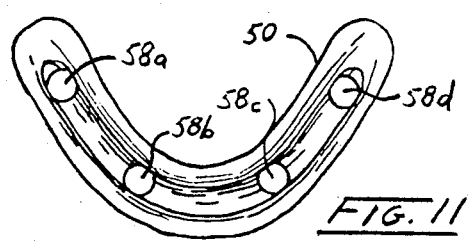
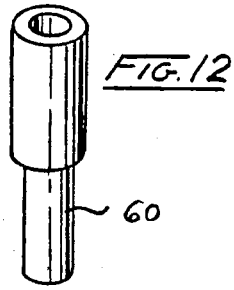
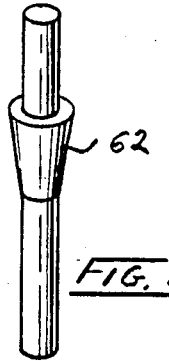
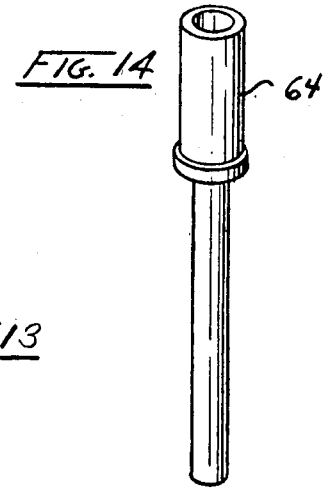

SUBPERIOSTEAL IMPANT WITH DETACHABLE BAR AND METHOD FOR ITS IMPLANTING

BACKGROUND OF THE INVENTION

The present invention generally relates to dentistry and more particularly to oral implantology.

The loss of permanent teeth by a person has resulted in the need for a denture to replace the natural teeth to assist the person in chewing as well as in proper functioning of the remaining natural teeth. Conventional dentures rest on the gingiva or gingival tissue and, where possible, have been anchored to existing natural teeth to maintain the denture in position. In cases where all of the teeth have been extracted from either the upper or lower jaw, or both, a full denture was utilized in direct contact with the gingival tissue at an appropriate time following extraction of the last natural teeth.

Although such dentures proved satisfactory, their ultimate success depended upon a variety of factors including the patient's perseverence and ability to tolerate the discomfort as well as the resulting diminished chewing capacity. Also, since the denture was resting on the gingival tissue, the mandible or maxillary bone resorbed which resulted in shrinkage of the tissue. Such tissue shrinkage, in turn, made it necessary to reline or rebase the denture in order to ensure a proper fit.

One solution to this problem which has been proposed in the field of dentistry involves endosseous and subperiosteal implants. These implants have been attached by a variety of techniques during surgery which include the opening of the gingival tissue followed by the securement of a frame member to the exposed bone. Thereafter, the gingival tissue was sutured and an impression made in the mouth. Dentures then could be custom manufactured for fitting into the patient's mouth by securement of the denture to the implanted frame member.

For example, U.S. Pat. No. 3,514,858 proposed to embed studs or posts into the bone so that a denture can be secured to such post. An improved endossius ramus implant is shown in U.S. Pat. No. 3,641,671. In U.S. Pat. No. 3,748,739, the implanted posts or studs are interconnected by bars for better securing the dentures thereto. U.S. Pat. No. 3,889,375 proposes a one-piece support for upper dentures. U.S. Pat. No. 4,202,099 is another form of a ramus implant. U.S. Pat. No. 4,253,833 relates to a technique for securing the stud or post implant wherein temporary caps are used during surgery, which caps later are replaced by a tooth-receiving head member. U.S. Pat. No. 4,370,134 relates to an upper denture support structure. U.S. Pat. No. 4,511,335 relates again to an improved endossius implant. Finally, U.S. Pat. No. 4,516,937 relates to a lower jaw dental prosthesis which relies on critical lengths and heights of an arcuate metal strip implant.

While all of these techniques have to some degree solved the problem of securing the denture directly in contact with the gingival tissue, improvement in this field of implantology still is required. For example, conventional subperiosteal implants make the suturing step of the surgery difficult since little room between the tissue and the denture securing bar exists. Another problem involves the difficulty in taking the impression due to the presence of the denture securing bar and the space between such bar and the sutured gingival tissue.

BROAD STATEMENT OF THE INVENTION

The present invention addresses such problems which have arisen due to the design of conventional subperiosteal and related dental implants. The dental implant of the present invention comprises a frame which is attachable to the mandible or maxillary bone and which frame bears bar retention means. The dental implant further comprises a detachable bar which has complementary bar retention means for removably attaching the detachable bar to the implanted frame. Finally, the implant comprises a denture which bears denture bar retention means for attaching the denture to the detachable bar.

The inventive method for implanting the dental implant comprises the following steps:

(a) exposing the mandible or maxillary bone by cutting the gingival tissue;
(b) attaching a frame to said exposed bone, said frame bearing bar retention means;
(c) suturing the cut gingival tissue;
(d) attaching a detachable bar to said frame, said bar having complementary bar retention means for disattaching;
(e) making an impression of said bar and gingival tissue;
(f) making a denture from said bar and impression, said denture bearing denture bar retaining means;
(g) re-attaching said bar to said implant; and
(h) attaching said denture to said bar.

Advantages of the present invention include the ability of the dentist to suture the cut gingival tissue in a much shorter time and with less difficulty. A further advantage is the ability of the dentist to take a superior impression. Yet another advantage is the ability of the dental lab to fashion a denture which fits much more securely to the bar due to the removal of the bar from the patient along with the impression. These and other advantages will be readily apparent to those skilled in the art based upon the disclosure contained herein.

BRIEF DESCRIPTION OF THE DRAWINGS

FIG. 1 is an exploded perspective view of a mandibular implant unconnected wherein the frame is attached to the mandible;

FIG. 2 is a perspective view of the dental implant of FIG. 1 wherein the denture and bar have been respectively attached to the implanted frame;

FIG. 3 is a cross-sectional elevational view taken along line 3—3 of the dental implant of FIG. 2;

FIG. 4 is a bottom plan view of the denture of FIG. 1;

FIG. 5 is an exploded perspective view of the dental implant like that in FIG. 1, but with alternative means for securing the components of the dental implant together;

FIG. 6 is a cross-sectional elevational view like FIG. 3, but is through the dental implant in FIG. 5;

FIG. 7 is a bottom plan view of the denture of FIG. 5;

FIG. 8 is a perspective view of an alternative detachable bar of the dental implant;

FIG. 9 is an exploded perspective view like FIGS. 1 and 5 of the dental implant; but depicts an alternative means for attaching the components of the dental implant together;

FIG. 10 is a cross-sectional elevational view like FIGS. 3 and 6, but is of the dental implant of FIG. 9;

FIG. 11 is a bottom plan view of the denture depicted in FIGS. 9 and 10;

FIGS. 12-14 are pieces which are utilized in the casting of the dental implant and in the manufacturing of a new denture for a dental implant when the original denture has been damaged;

Figure 15:
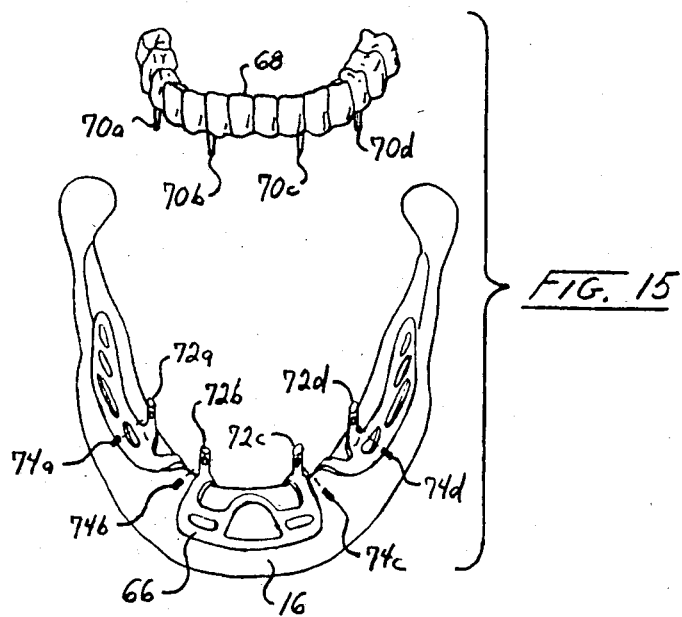
FIG. 15 is an exploded perspective view like FIGS. 1, 5, and 9 of the dental implant, but depicts the use of a fixed bridge in place of the denture.

The drawings will be described in detail in connection with the description of the invention which follows.

DETAILED DESCRIPTION OF THE INVENTION

The dental implant of the present invention is beneficial to the dental surgeon who performs the implant surgery, the dental laboratory which fashions the implant and dentures, and the patient who receives the dental implant. For the dentist, suturing the gingival tissue after insertion of the implant frame is a much easier task since the bar is not affixed to the frame. This means that less time is required for the patient to be sedated. Next, the dental surgeon can make an impression (e.g. with plaster of Paris, polymeric materials, etc.) much easier since the bar is removed from the frame along with the impression. With a permanent bar, difficulty always is encountered with the impression material becoming lodged between the bar and the sutured gingival tissue. Since the bar is removed with the impression, no such difficulties are encountered with the inventive implant.

Next, the dental laboratory can fashion a denture which is much tighter fitting with the bar and gingival tissue since the bar is present in the laboratory during the denture manufacturing operation. This results in a much better fit of the denture which pleases the patient. Installation of the bar for permanence is accomplished easily by the dental surgeon prior to the patient being finally fitted with the custom-manufactured dental implant.

For a fuller understanding of the inventive dental implant, reference is made to the accompanying drawings which illustrate the inventive dental implant. Referring to FIG. 1, the three basic elements comprising the dental implant are set forth in an exploded, perspective view. These three major components comprise denture 10, detachable bar 12, and frame 14 which is attached to mandible 16. It should be recognized that frame 14 also can be attached to the maxillary bone in conventional fashion. In the embodiment set forth in FIG. 1, frame 14 bears four bar retention means 18a-18d. Bar retention means 18 are sleeve-like (annular) members or female connectors. Detachable bar 12 bears four complementary bar retention means 20a-20d for removably attaching detachable bar 12 to frame 16 via frame bar retention means 18a-18d, respectively. Complementary bar retention means 20a-20d are cylindrical-like projections or male attaching means which mutually engage frame bar retention means 18a-18d in conventional fashion. Permanent connection between detachable bar 12 and frame 14 can be accomplished by use of conventional dental cements. Alternatively, close-tolerance friction fitting between frame bar retention means 18a-18d and detachable bar complementary bar retention means 20a-20d can permit future detachability of detachable bar 12 as is necessary, desirable, or convenient.

The dental implant of FIG. 1 is shown assembled in FIG. 2 with no gingival tissue being shown. FIGS. 3 and 4 show how detachable bar 12 is attached to denture 10. From FIG. 4, it will be observed that denture 10 bears three elongate clips 24a-24c for press fitting detachable bar 12 thereinto. These clips desirably are made from plastic, though other materials of construction, e.g. polymeric, metallic, or like materials, can be used alternatively. Such press-fitting arrangement is set forth at FIG. 3 for clip 24b. Also shown is the insertion of peg 20c into female connector 18c for affixing detachable bar 12 to frame 14. Also shown at FIG. 3 in phantom is the location of gingival tissue 22. It should be noted that the number of frame bar retention means 18 and complementary bar retention means 20 can be present in a number other than four as depicted in FIG. 1. For that matter, other means of securing frame 14 to mandible 16 will be readily apparent to those skilled in this art, e.g. such as those discussed in the art cited above.

A variety of alternative means exist for attaching the basic components of the dental implant. For example, FIG. 5 shows a dental implant compising denture 26, detachable bar 28, and frame 30 which is affixed to mandible 16. In this alternative embodiment, frame 30 bears four male-connecting bar retention means 32a-32d. Detachable bar 28 bears four complementary bar retention means 34a-34d which are female-like connectors. Thus, it will be observed that the male/female connecting system between the detachable bar and the frame may be reversed between that depicted at FIG. 1 and that depicted at FIG. 5.

FIGS. 5-7 also illustrate another means for attaching detachable bar 28 to denture 26. It will be observed that detachable bar 28 bears four protrusions which terminate with ball-like ends. These ball-like ends fit within O-rings 38a-38d as depicted at FIG. 7. The cross-sectional view of such attaching system is set forth at FIG. 6 (in the same manner as that described in connection with FIG. 3). As was true with the dental implant embodiment of FIG. 1, the number of retention means on denture 26, detachable bar 28, and frame 30 can be more or less in number than the number set forth in FIGS. 5-7.

Detachable bars 12 and 28 are seen to extend about the full circumference of mandible 16 and dentures 10 and 26, respectively. Alternative embodiments for the detachable bar exist, such as set forth at FIG. 8. In FIG. 8, frame 40 affixed to mandible 16 bears a pair of unilateral detachable bars 42 and 44. The ball/O-ring means of affixing unilateral bars 42 and 44 to denture 26 are depicted at FIG. 8. It should be appreciated that alternative means for attaching unilateral bars 42 and 44 to denture 26 could be accommodated by such unilateral bars. Besides the unilateral bar embodiment set forth at FIG. 8, frame 40 easily could bear an anterior (front) bar. Thus, non-continuous or segmented bar arrangements, such as that bilateral bar arrangement depicted at FIG. 8, can be adapted for the inventive dental implant is is necessary, desirable, or convenient.

Yet another alternative embodiment for the inventive dental implant is set forth at FIG. 9. The dental implant of FIG. 9 comprises frame 46 which is attached to mandible 16, detachable bar 48, and denture 50. Frame 46 bears four internally-threaded posts 52a–52d. Detachable bar 48 has four complementary holes 54a–54d which fit about the upper ends of internally-threaded posts 52a–52d. Detachable bar 48 then is affixed to frame 46 via screws 56a–56d which penetrate through holes 54a–54d, respectively, of frame 48 and thence into posts 52a–52d, respectively, of frame 46. For that matter, denture 50 easily could be adapted so that screws 56a–56d simultaneously penetrated through denture 50 and detachable bar 48 for securing both of them to frame 46.

FIGS. 10 and 11 depict yet another means for affixing denture 50 to detachable bar 48. From FIG. 11, it will be observed that denture 50 bears magnets 58a–58d. Such magnets may be used when detachable bar 48 is manufactured from a magnetic material or when magnets are attached (e.g. by soldering) to bar 48. Attachment, then, would be accomplished as set forth in the cross-sectional view depicted at FIG. 10. Of course, the number of screws 56 and magnets 58 may be different than the number set forth in FIGS. 9 and 11. For that matter, a continuous magnet retained within the recess of denture 50 may find use for attaching denture 50 to detachable bar 48. Further, it will be appreciated that the various alternative attaching means of the frame, detachable bar, and denture of the novel dental implant may be mixed in various fashions from those embodiments set forth in the drawings, or from other embodiments that may be apparent to those skilled in the art based upon the disclosure contained herein.

Figure 16:
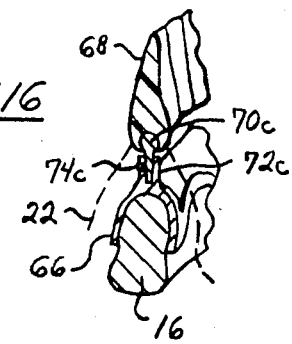
FIG. 16 is a cross-sectional elevational view like FIG. 3 of the dental implant of FIG. 15.
Figure 17:
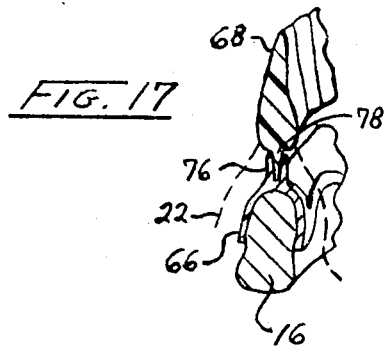
FIG. 17 is a cross-sectional elevational view like FIG. 16, but with an alternative means for securing the components of the dental implant together.

Another advantage realized by the unique detachable construction of the inventive implant revolves around the detachability of the bar. For example, a patient initially may desire a denture be fitted with the implant utilizing the detachable bar inventive implant. Later, however, the patient may opt for the fitting of a fixed bridge to replace the denture. In such circumstances, the inventive implant readily can be adapted for accommodating a fixed bridge. This is possible only because the bar is detachable. With respect to FIG. 15, it will be observed that the detachable bar has been removed from frame 66. With the bar removed, the implant readily converts for accommodating fixed bridge 68 which bears attachment members 70a–70d. These attachment members fit into sleeves 72a–72d, respectively. The noted sleeves have holes which penetrate therethrough (shown in the front, but may be as readily sited on the back side of such sleeves) which accommodate screws 74a–74d for securing fixed bridge 68 with frame 66. A cross-sectional elevational view for this means of attachment can be viewed at FIG. 16. Alternatively, integrally formed posts as depicted at FIG. 17 can be manufactured into fixed bridge 68 wherein sleeve 76 for integrally formed post 78 is set forth. Of course, the detachable bar easily could be embedded in denture 68 in the same manner it has been described with reference to the denture embodiment of the present invention.

Figure 18:
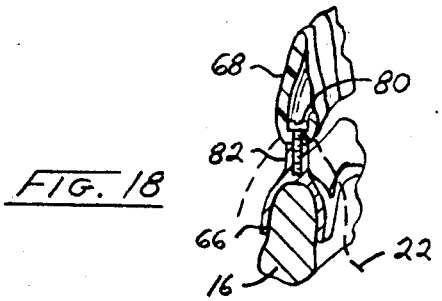
FIG. 18 is a cross-sectional elevational view like FIG. 16, but with alternative means for securing the components of the dental implant together.

Finally, it will be observed at FIG. 18 that screws, like screw 80 as depicted, can be used to simultaneously secure fixed bridge 68 to frame 66 via internally threaded sleeve 82 of frame 66. Those skilled in the art will appreciate that even further modes of attachment of the various components of the inventive implant may be envisioned based upon the precepts of the present invention. Regardless of the mode of attachment, the provision of a detachable bar retains the conventional benefits of an implant with added improvements in its implanting into the patient while providing the flexibility for accommodating a variety of dental prosthesis.

It further will be appreciated that the various frame bar retention means may be submergable (below the gingival tissue) or they may protrude above the gingival tissue as set forth in the drawings. Further, denture 10 may be a fixed or removable bridge, a conventional denture, or other dental prosthesis.

The method for implanting the inventive dental implant is accomplished in a fashion similar to, but different than, conventional implant methodologies. Initially, the dental surgeon must fashion a bone impression of the mandible or maxillary bone by directly taking an impression after cutting the gingival tissue, or such bone impression may be fashioned based on a CAT scan which is a digitally-accurate, threedimensional custom manufactured model for surgical planning use by dental implantologists. Regardless of the technique employed, a negative bone impression is presented to the dental laboratory. The dental laboratory can make a positive model poured from dental stone (a convention dental gypsum product) so that the frame design can be created thereon. Next, the dental laboratory will fashion a refractory model of the frame and then make a wax master model. In this wax master model, clip 62 (FIG. 13) can be used to create female posts 18a–18d of frame 14 (FIG. 1). Similarly, pin 64 of FIG. 14 can be used to fashion posts 20a–20d of detachable bar 12.

Next, based upon the wax master model, an investment mold is made and the final parts cast from an appropriate metal. Appropriate metals for fashioning the dental implant include surgical cobalt-chromium alloys (e.g. surgical Vitallium brand cobalt-chromium alloy denture, Austenal Products Laboratory), surgical titanium, gold, silver, or like surgical metals. Clips 60–64 of FIGS. 12–14 desirably will be manufactured from plastic, though other materials of construction including polymeric, ceramic, and metallic materials may be used as is necessary, desirable, or convenient.

With the frame and detachable bar now made by the so-called "lost wax" process, the dental surgeon can attach the frame to the mandibular bone or maxillary bone. Next, the dental surgeon sutures (suturing being used generically herein to include stapling, clamping, or other means of reattaching the cut tissue) the cut gingival tissue. In this suturing operation, the detachable bar is not attached to frame 14 so that there is no obstruction presented to the dental surgeon in accomplishing the suturing procedure. Next, the dental surgeon takes an impression (utilizing plaster, a polymeric material, or the like) of the gingival tissue wherein the detachable bar has been inserted into the implanted frame. The dental surgeon them removes the impression which contains the detachable bar for transmission to a dental laboratory. The dental laboratory then utilizes the impression for fashioning the appropriate denture. The dental laboratory can fashion a denture which has a truer fit to the detachable bar because the detachable bar is present in the laboratory during the denture-manufacturing procedure, rather than in the mouth of the patient permanently attached to the implanted frame. Finally, the detachable bar and denture are returned to the dental surgeon for final insertion into the patient's mouth. As noted above, the detachable bar may be removably-fitted into the frame or may be permanently attached to the frame by use of dental cement, screws, or like techniques as described above. Regardless of the embodiment of the novel dental implant, the procedure has been simplified with a much improved dental implant compared to those dental implants presently on the market.

A final unique feature of the novel dental implant is the use of piece 60 of FIG. 12. This piece is used when a person bearing the novel dental implant has the denture and detachable bar damaged due to an accident or like occurrence. Piece 60 is inserted into one of the female posts 18 (FIG. 1) for taking a new impression the patient's mouth. The detachable bar then can be made based upon the dental impression since the corresponding post is part of the impression. Thus, a "retrofitting" procedure for the novel dental implant has been designed into its structure.

It will be appreciated that the novel dental implant has flexibility to be adapted to a variety of patients and situations. Its unique construction and function make it a significant advancement in the dental implant field. Further adaptations and embodiments of the novel dental implant will be readily apparent to those skilled in the art based on the disclosure contained herein. In this application, all citations are expressly incorporated herein by reference.

I claim:

1. A subperiosteal dental implant for a denture which comprises:
    (a) a frame which is shaped to conform to and cradle around and attachable to the mandibular or maxillary bone, said frame bearing solid or annular post bar retention means;
    (b) a detachable bar having complementary interfitting solid or annular post bar retention means for removably attaching said detachable bar to said frame, said bar being adapted for removal from said frames; and
    (c) a denture bearing denture bar retention means for attaching said denture to said detachable bar, said denture fashioned from an impression which contains said detachable bar.

2. The dental implant of claim 1 which is made from materials selected from the group consisting of metal or ceramic material.

3. The dental implant of claim 2 wherein said dental implant is manufactured from metal selected from the group consisting of gold, silver, titanium, cobalt-chromium alloys, or combinations thereof.

4. The dental implant of claim 1 wherein said frame bar retention means comprise annular posts.

5. The dental implant of claim 1 wherein said frame bar retention means comprise solid posts.

6. The dental implant of claim 4 wherein said annular posts are internally threaded.

7. The dental implant of claim 4 wherein said complementary bar retention means of said detachable bar comprise solid posts which fit into said annular frame bar retention posts.

8. The dental implant of claim 5 wherein said complementary bar retention means of said detachable bar comprise annular posts which fit about said frame bar retention solid posts.

9. The dental implant of claim 1 wherein said detachable bar additionally contains upper posts which are terminated with rounded ends.

10. The dental implant of claim 6 wherein said detachable bar has holes which penetrate therethrough and said dental implant additionally comprises screws which penetrate through said holes in said detachable bar for screwing into said internally threaded annular posts on said frame.

11. The dental implant of claim 1 wherein said denture bar retention means comprises elongate clips for press fitting said detachable bar thereinto.

12. The dental implant of claim 9 wherein said dental bar retention means comprise O-rings for receiving said rounded ends of said posts.

13. The dental implant of claim 1 wherein said detachable bar is manufactured from metallic material and said denture bar retention means comprise magnet means.

14. The dental implant of claim 1 which comprises a plurality of detachable bars.

15. The dental implant of claim 1 wherein said bar retention means of said frame are submergable.

16. The dental implant of claim 8 wherein a screw fits transversely into said annular post for retaining said frame bar retention solid post.

17. The dental implant of claim 1 where, after its implanting into the mouth of a person, said detachable bar is replaced by a dental prosthesis having complementary retention means for attaching said prosthesis to said frame.

18. Method for implanting a subperiosteal dental implant which comprises:
    (a) exposing a mandible or maxillary bone by cutting the gingival tissue;
    (b) attaching a frame to said exposed bone, said frame shaped to conform to and cradle around the exposed bone and bearing solid or annular post bar retention means;
    (c) suturing the cut gingival tissue;
    (d) attaching a detachable bar to said frame, said bar having complementary interfitting solid or annular post bar retention means for this attaching;
    (e) making an impression of said bar and gingival tissue;
    (f) making a denture from said bar and impression, said denture bearing denture bar retention means;
    (g) re-attaching said bar to said implant; and
    (h) attaching said denture to said bar.

19. The method of claim 18 wherein said re-attaching of step (g) is accomplished by cementing said bar to said implant.

20. The method of claim 18 wherein said dental implant comprises the dental implant of claim 7.

21. The method of claim 18 wherein said dental implant comprises the dental implant of claim 8.

22. The method of claim 18 wherein said dental implant comprises the dental implant of claim 12.

23. The method of claim 18 wherein for step (g) said bar is replaced by a dental prosthesis which is attached to said frame.

* * * * *